(12) United States Patent
Hancock et al.

(10) Patent No.: US 12,064,175 B2
(45) Date of Patent: Aug. 20, 2024

(54) ELECTROSURGICAL INSTRUMENT

(71) Applicant: CREO MEDICAL LIMITED, Chepstow (GB)

(72) Inventors: Christopher Paul Hancock, Bath (GB); Patrick Burn, Chepstow (GB); Pallav Shah, Chepstow (GB)

(73) Assignee: CREO MEDICAL LIMITED, Chepstow (GB)

( * ) Notice: Subject to any disclaimer, the term of this patent is extended or adjusted under 35 U.S.C. 154(b) by 792 days.

(21) Appl. No.: 17/256,588

(22) PCT Filed: Jul. 27, 2019

(86) PCT No.: PCT/EP2019/067168
§ 371 (c)(1),
(2) Date: Dec. 28, 2020

(87) PCT Pub. No.: WO2020/011547
PCT Pub. Date: Jan. 16, 2020

(65) Prior Publication Data
US 2021/0267681 A1  Sep. 2, 2021

(30) Foreign Application Priority Data

Jul. 12, 2018  (GB) ..................... 1811433

(51) Int. Cl.
*A61B 18/18* (2006.01)
*A61B 18/00* (2006.01)

(52) U.S. Cl.
CPC ............ *A61B 18/1815* (2013.01); *A61B 2018/00083* (2013.01); *A61B 2018/00577* (2013.01);

(Continued)

(58) Field of Classification Search
CPC ...... A61B 18/1815; A61B 2018/00083; A61B 2018/00577; A61B 2018/00982;
(Continued)

(56) References Cited

U.S. PATENT DOCUMENTS 5,405,346 A  4/1995  Grundy et al.
5,904,709 A  5/1999  Arndt et al.
(Continued)

FOREIGN PATENT DOCUMENTS

GB       2403148 A         12/2004
JP       2009-006150 A      1/2009
WO   WO 2012/095654 A1     7/2012

OTHER PUBLICATIONS

International Preliminary Report on Patentability issued by the International Searching Authority in corresponding Application No. PCT/EP2019/067168, dated May 29, 2020.
(Continued)

*Primary Examiner* — Khadijeh A Vahdat
(74) *Attorney, Agent, or Firm* — ArentFox Schiff LLP

(57) ABSTRACT

An electrosurgical instrument for delivering microwave energy to biological tissue, in which a pair of conductive tuning elements are mounted in a radiating instrument tip to shape a microwave radiation profile of the instrument so that the radiation profile is constrained around the instrument tip. Such tuning elements may result in a radiation profile that is substantially spherical around the instrument tip, providing a well-defined ablation volume. The tuning elements act to improve the efficiency with which microwave energy can be delivered into target tissue.

19 Claims, 15 Drawing Sheets

(52) U.S. Cl.
CPC ............... *A61B 2018/00982* (2013.01); *A61B 2018/1823* (2013.01); *A61B 2018/1853* (2013.01); *A61B 2018/1861* (2013.01); *A61B 2018/1892* (2013.01)

(58) Field of Classification Search
CPC .... A61B 2018/1823; A61B 2018/1853; A61B 2018/1861; A61B 2018/1892
See application file for complete search history.

(56) References Cited

U.S. PATENT DOCUMENTS

| | | | |
|---|---|---|---|
| 2001/0008966 A1 | 7/2001 | Arndt et al. | |
| 2011/0282336 A1* | 11/2011 | Brannan | A61B 18/1815 606/33 |
| 2016/0000505 A1 | 1/2016 | Cronin | |
| 2017/0172656 A1 | 6/2017 | Brannan et al. | |

OTHER PUBLICATIONS

International Search Report and the Written Opinion issued by the International Searching Authority corresponding to International Application No. PCT/EP2019/067168, dated Oct. 2, 2019.
Search Report issued by the British Patent Office in corresponding British Application No. 1811433.0, dated Dec. 20, 2018.

* cited by examiner

ELECTROSURGICAL INSTRUMENT

CROSS-REFERENCE TO RELATED APPLICATIONS

This application is a National Stage entry of International Application No. PCT/EP2019/067168, filed on Jun. 27, 2019, which claims priority to British Patent Application No. 1811433.0, filed on Jul. 12, 2018. The disclosures of the priority applications are hereby incorporated in their entirety by reference.

FIELD OF THE INVENTION

The invention relates to an electrosurgical instrument for delivering microwave energy to biological tissue in order to ablate the tissue. The instrument may comprise a probe that is insertable through a channel of an endoscope or catheter, or may be used in laparoscopic surgery or open surgery. The instrument may be used in pulmonary or gastrointestinal applications, but is not limited to such.

BACKGROUND TO THE INVENTION

Electromagnetic (EM) energy, and in particular microwave energy, has been found to be useful in electrosurgical operations for its ability to ablate biological tissue. Typically, apparatus for delivering EM energy to body tissue includes a generator comprising a source of EM energy, and an electrosurgical instrument connected to the generator, for delivering the energy to tissue.

Conventional electrosurgical instruments are often designed to be inserted percutaneously into the patient's body. However, it can be difficult to locate the instrument percutaneously in the body, for example if the target site is in a moving lung or a thin walled section of the gastrointestinal (GI) tract. Other electrosurgical instruments can be delivered to a target site by a surgical scoping device (e.g. an endoscope) which can be run through channels in the body such as airways or the lumen of the oesophagus or colon. This allows for minimally invasive treatments, which can reduce the mortality rate of patients and reduce intraoperative and postoperative complication rates.

Tissue ablation using microwave EM energy is based on the fact that biological tissue is largely composed of water. Human soft organ tissue is typically between 70% and 80% water content. Water molecules have a permanent electric dipole moment, meaning that a charge imbalance exists across the molecule. This charge imbalance causes the molecules to move in response to the forces generated by application of a time varying electric field as the molecules rotate to align their electric dipole moment with the polarity of the applied field. At microwave frequencies, rapid molecular oscillations result in frictional heating and consequential dissipation of the field energy in the form of heat. This is known as dielectric heating.

This principle is harnessed in microwave ablation therapies, where water molecules in target tissue are rapidly heated by application of a localised electromagnetic field at microwave frequencies, resulting in tissue coagulation and cell death. It is known to use microwave emitting probes to treat various conditions in the lungs and other organs. For example, in the lungs, microwave radiation can be used to treat asthma and ablate tumours or lesions.

SUMMARY OF THE INVENTION

At its most general, the invention provides an electrosurgical instrument for delivering microwave energy to biological tissue, in which a pair of conductive tuning elements are used to shape a microwave radiation profile of the instrument so that the radiation profile (also referred to as an "ablation profile") is constrained around the instrument tip. The inventors have found that using such tuning elements may result in a radiation profile that is substantially spherical around the instrument tip, providing a well-defined ablation volume. The inventors have also found that the tuning elements may act to improve the efficiency with which microwave energy can be delivered into target tissue.

According to a first aspect of the invention, there is provided an electrosurgical instrument comprising: a coaxial feed cable for conveying microwave energy, the coaxial feed cable having an inner conductor, an outer conductor, and a dielectric material separating the inner conductor and the outer conductor; and a radiating tip disposed at a distal end of the coaxial feed cable to receive the microwave energy, the radiating tip comprising: an elongate conductor electrically connected to the inner conductor and extending in a longitudinal direction to form a microwave radiator; a proximal tuning element electrically connected to the elongate conductor in a proximal region of the radiating tip; a distal tuning element electrically connected to the elongate conductor in a distal region of the radiating tip; and a dielectric body disposed around the elongate conductor, the proximal tuning element and the distal tuning element, wherein the proximal tuning element and the distal tuning element are spaced apart in the longitudinal direction, whereby a microwave field emitted by the microwave radiator is shaped around the dielectric body.

The instrument may operate to ablate target tissue in the body. The device is particularly suited to the ablation of tissue in the lungs, however it may be used to ablate tissue in other organs (e.g. the uterus or the GI tract). In order to efficiently ablate target tissue, the radiating tip should be located as close as possible (and in many cases inside) the target tissue. In order to reach the target tissue (e.g. in the lungs), the device may need to be guided through passageways (e.g. airways) and around obstacles. This means that the instrument will ideally be as flexible as possible and have a small cross section. Particularly, the device should be very flexible near its tip, where it may need to be steered along narrow passageways such as bronchioles which can be narrow and winding.

The coaxial feed cable may be a conventional low loss coaxial cable that is connectable at one end to an electrosurgical generator. In particular, the inner conductor may be an elongate conductor extending along a longitudinal axis of the coaxial feed cable. The dielectric material may be disposed around the inner conductor, e.g. the first dielectric material may have a channel through which the inner conductor extends. The outer conductor may be a sleeve made of conductive material that is disposed on the surface of the dielectric material. The coaxial feed cable may further include an outer protective sheath for insulating and protecting the cable. In some examples, the protective sheath may be made of or coated with a non-stick material to prevent tissue from sticking to the cable. The radiating tip is located at the distal end of the coaxial feed cable, and serves to deliver EM energy conveyed along the coaxial feed cable into target tissue. The radiating tip may be permanently attached to the coaxial feed cable, or it may be removably attached to the coaxial feed cable. For example, a connector may be provided at the distal end of the coaxial feed cable, which is arranged to receive the radiating tip and form the required electrical connections.

The radiating tip may be generally cylindrical. The dielectric body may be attached to a distal end of the coaxial feed cable. In some examples, the dielectric body may comprise a protruding portion of the dielectric material of the coaxial feed cable that extends beyond the distal end of the coaxial feed cable. This may simplify construction of the radiating tip, and avoid reflections of EM energy at the boundary between the radiating tip and the coaxial feed cable. In other examples, a second dielectric material, different from the dielectric material of the coaxial feed cable may be used to form the dielectric body. The second dielectric material may be selected to improve impedance matching with target tissue in order to improve the efficiency with which the microwave energy is delivered into target tissue. The radiating tip may also include multiple different pieces of dielectric material, which are selected and arranged to shape the radiation profile in a desired manner.

The elongate conductor is electrically connected to the inner conductor of the coaxial feed cable and extends within the dielectric body so that it acts as a microwave radiator. In other words, microwave energy conveyed to the radiating tip from the coaxial feed cable may be radiated from the elongate conductor. The outer conductor may terminate at the distal end of the coaxial feed cable, such that the elongate conductor extends beyond a distal end of the outer conductor. In this manner, the radiating tip may act as a microwave monopole antenna. Thus, microwave energy conveyed to the radiating tip may be radiated from the elongate conductor into surrounding target tissue. The elongate conductor may, for example, extend within a channel in the dielectric body. The elongate conductor may be any suitable conductor having an elongate shape. For example, the elongate conductor may be a wire, rod or strip of conductive material that extends within the dielectric body.

The proximal tuning element may be a piece of conductive material (e.g. metal) that is located near a proximal end of the radiating tip. The distal tuning element may be a piece of conductive material (e.g. metal) that is located near a distal end of the radiating tip. Thus, the distal tuning element may be further away from the distal end of the coaxial feed cable than the proximal tuning element. The proximal and distal tuning elements are both electrically connected to the elongate conductor. For example, the proximal and distal tuning elements may each be disposed on or around the elongate conductor. The proximal and distal tuning elements may be electrically connected to the elongate conductor by any suitable means. For example, the proximal and distal tuning elements may be welded or soldered to the elongate conductor. In another example, the proximal and distal tuning elements may be connected to the elongate conductor using a conductive adhesive (e.g. conductive epoxy). Alternatively, one or both of the proximal and distal tuning elements may be integrally formed with the elongate conductor (e.g. they may be manufactured together as a single piece). The proximal and distal tuning elements are spaced apart in a longitudinal direction by a length of the elongate conductor. In other words, a section of the elongate conductor is disposed between the proximal and distal electrodes. The proximal and distal tuning elements may be covered by a portion of the dielectric body, so that they are isolated/protected from the environment.

The inventors have found that a radiating tip having a configuration as described above may reduce an impedance mismatch between the radiating tip and surrounding target tissue. This may reduce the amount of microwave energy that is reflected back down the coaxial feed cable at the radiating tip (which occurs due to impedance mismatch between the radiating tip and the target tissue). As a result, the efficiency with which microwave energy can be delivered into target tissue may be improved. This may enable the amount of energy that needs to be conveyed down the coaxial feed cable to ablate target tissue to be reduced. This may in turn reduce heating effects due to transmission of microwave energy along the coaxial feed cable, such that the electrosurgical instrument may be used for longer periods of time.

The inventors have also found that the proximal and distal tuning elements may result in a more desirable radiation profile of the radiating tip. In particular, the tuning elements may shape the radiation profile such that it is concentrated around the radiating tip, and reduce a tail of the radiation profile that extends back along the coaxial feed cable. In this manner, microwave energy conveyed to the radiating tip may be emitted from the radiating tip and ablate surrounding target tissue in a well-defined volume around the radiating tip. The ablation volume (i.e. a volume of tissue that is ablated by the radiated microwave energy) may be approximately spherical. The shape, size and location of the tuning elements may be selected to obtain a desired microwave radiation profile.

The proximal tuning element and the distal tuning element may be disposed symmetrically with respect to the longitudinal direction. For example, the proximal tuning element and the distal tuning element may be cylindrical, e.g. having a central axis that is collinear with a longitudinal axis of the elongate conductor. The longitudinal axis of the elongate conductor is an axis along the length of the elongate conductor. For example, the proximal tuning element may be a cylindrical piece of conductive material disposed around, and coaxial with, the elongate conductor. This may improve the axial symmetry of the radiation profile of the radiating tip.

In some embodiments, the proximal tuning element may be spaced from the distal end of the coaxial feed cable in the longitudinal direction. For example, the dielectric body may include a spacer which is positioned between the distal end of the coaxial feed cable and the proximal tuning element. The inventors have found that spacing the proximal tuning element from the distal end of the coaxial feed cable may introduce a phase shift into the instrument. The phase shift may improve impedance matching between the radiating tip and target tissue, so that efficiency of microwave energy into target tissue may be improved. The phase shift may depend on the distance between the distal end of the coaxial feed cable and a proximal end of the proximal tuning element.

In some embodiments, the proximal tuning element may include a channel for receiving the elongate conductor. The channel may serve to position the proximal tuning element relative to the elongate conductor, and improve the connection between the proximal tuning element and the elongate conductor. The channel may also facilitate assembly of the radiating tip, as the proximal tuning element may be positioned on the elongate conductor at the desired position, before securing the proximal tuning element to the elongate conductor. The channel may be a closed channel (e.g. a tunnel) that passes through the proximal tuning element. In this manner, the proximal tuning element may be disposed around the elongate conductor. This may improve the axial symmetry of the radiating tip's radiation profile. For example, where the proximal tuning element has a cylindrical shape, the channel may extend along the central axis of the cylinder. Alternatively, the channel may be an open channel, e.g. it may be a groove extending along a surface of the proximal tuning element. The proximal tuning element may be electrically connected to the elongate conductor in the channel in the proximal tuning element. For example, a wall of the channel may be in direct contact with an outer surface of the elongate conductor. In addition or alternatively, the proximal tuning element may be secured to the elongate conductor within the channel (e.g. using a conductive adhesive, solder joins or welding joins).

Similarly, the distal tuning element may include a channel for receiving the elongate conductor. The channel in the distal tuning element may have any of the properties discussed above in relation to the channel in the proximal tuning element. In particular, the channel may be open or closed, and the distal tuning element may be electrically connected and/or secured to the elongate conductor in the channel in the distal tuning element.

In some embodiments, the distal tuning element may be located at a distal end of the elongate conductor. Thus, the distal tuning element may be located at the end of the elongate conductor which is furthest away from the coaxial feed cable. This may serve to concentrate the radiation profile around the distal end of the radiating tip. This may result in a more spherical radiation pattern. For example, the elongate conductor may terminate at/near the distal tuning element. In some examples, the elongate conductor may not protrude beyond a distal end of distal tuning element. Where the distal tuning element includes a channel, the elongate conductor may terminate inside or at a distal end of the channel, such that it does not protrude from the distal end of the channel. In some cases, the channel may not extend along the whole length of the distal tuning element, such that the elongate conductor terminates within the distal tuning element. In this manner, the distal tuning element may form a cap on the distal end of the elongate conductor.

In some embodiments, a length of the distal tuning element in the longitudinal direction may be greater than a length of the proximal electrode in the longitudinal direction. The longitudinal direction corresponds to the direction in which the elongate conductor extends. This may serve to concentrate radiation around the distal end of the radiating tip, which may result in a more spherical radiation patter. For example, the distal tuning element may be twice as long as the proximal tuning element in the longitudinal direction.

In some embodiments, the elongate conductor may be a distal portion of the inner conductor that extends beyond the distal end of the coaxial feed cable. In other words, the inner conductor may extend beyond the distal end of the coaxial feed cable and into the dielectric body to form the elongate conductor. This may facilitate forming the radiating tip at the distal end of the coaxial feed cable, as it avoids having to connect a separate conductor to the distal end of the inner conductor.

In some embodiments, the dielectric body may include a dielectric spacer between the proximal tuning element and the distal tuning element. The dielectric spacer may include a channel through which a portion of the elongate conductor located between the proximal and distal tuning elements extends. The dielectric spacer may include a proximal face which is in contact with the proximal tuning element, and a distal face which is in contact with the distal tuning element.

In some embodiments, the dielectric body further comprises a dielectric sheath that surrounds an outer surface of the proximal tuning element and the distal tuning element. The dielectric sheath may provide an outer protective layer for protecting the radiating tip from the environment. For example, the dielectric sheath may be made of or coated with a non-stick material (e.g. PTFE), so that tissue does not stick to the dielectric body. An outer surface of the dielectric sheath may be flush with an outer surface of the coaxial feed cable at an interface between the coaxial feed cable and the radiating tip.

As mentioned above, the proximal tuning element may be spaced from the distal end of the coaxial feed cable. A dielectric element may be disposed between the proximal tuning element and a distal end of the coaxial feed cable. The dielectric element may be a distal portion of the dielectric material of the coaxial feed cable that protrudes beyond a distal end of the outer conductor. This can assist in ensuring a smooth and secure physical and electrical connection between the coaxial feed cable and radiating tip. However, it need not be essential. The dielectric element may be a separate element, e.g. made from a different material from the dielectric material of the coaxial feed cable.

In some embodiments, the radiating tip may further include a distal tip mounted at a distal end of the elongate conductor, the distal tip being made of a dielectric material. The distal tip may be made of the same dielectric material as the dielectric body. Alternatively, the distal tip may be made of a different dielectric material from the rest of the dielectric body. The dielectric material of the distal tip may be selected to improve impedance matching between the radiating tip and target tissue. The distal tip may be pointed to facilitate insertion of the radiating tip into biological tissue. In other cases, the distal tip may be rounded. The distal tip may include a non-stick material (e.g. PTFE) on its outer surface, to prevent tissue from sticking to it.

In some embodiments, the electrosurgical instrument may further include a conductive field shaping element disposed at a distal end of the coaxial feed cable, the field shaping element being electrically connected to the outer conductor. The field shaping element may serve to reduce back-propagation of microwave energy down the coaxial feed cable. This may reduce a tail of the radiation profile that extends along a portion of the coaxial feed cable. As a result, the radiation profile may be concentrated around the radiating tip. The inventors have found that the tail in the radiation profile may be more pronounced on electrosurgical instruments having larger diameters. The field shaping element may therefore be particularly useful for electrosurgical instruments having larger outer diameters (e.g. greater than 2.0 mm).

The field shaping element may be made of any suitable conductive material. The field shaping element may be disposed on a surface of the outer conductor, e.g. on an outer surface or an inner surface of the outer conductor. The field shaping element may be electrically connected to the outer conductor via any suitable means, e.g. via a conductive epoxy, or via a soldered or welded connection. In some cases, the field shaping element may be integrally formed with a distal portion of the coaxial feed cable.

The field shaping element may serve to increase an effective thickness of the outer conductor in a distal portion of the outer conductor. In some cases, the field shaping element may be arranged symmetrically with respect to the longitudinal direction. This may serve to provide an axially symmetrical radiation profile. For example, the field shaping element may be an annular sleeve of conductive material disposed around an outer surface of the outer conductor.

In some embodiments, the field shaping element may be formed by a distal portion of the outer conductor having an increased thickness compared to a proximal portion of the outer conductor. In other words, the thickness of the outer conductor may be greater in the distal portion than in the proximal portion.

In some embodiments, the field shaping element may have a length in the longitudinal direction corresponding to a quarter wavelength of the microwave energy. In other words, the field shaping element may extend along a distal portion of the outer conductor having a length equivalent to a quarter wavelength of the microwave energy conveyed by the coaxial feed cable. This may serve to minimise back-propagation of microwave energy back down the coaxial feed cable, to improve the efficiency of energy delivery by the radiating tip.

The electrosurgical instrument discussed above may form part of a complete electrosurgical apparatus for treating biological tissue. For example, the apparatus may include an electrosurgical generator arranged to supply microwave energy; and the electrosurgical instrument of the invention may be connected to receive the microwave energy from the electrosurgical generator. The electrosurgical apparatus may further include a surgical scoping device (e.g. an endoscope) having a flexible insertion cord for insertion into a patient's body, wherein the flexible insertion cord has an instrument channel running along its length, and wherein the electrosurgical instrument is dimensioned to fit within the instrument channel.

In this specification "microwave" may be used broadly to indicate a frequency range of 400 MHZ to 100 GHz, but preferably the range 1 GHz to 60 GHz. Preferred spot frequencies for microwave EM energy include: 915 MHz, 2.45 GHz, 3.3 GHZ, 5.8 GHz, 10 GHz, 14.5 GHz and 24 GHz. 5.8 GHz may be preferred.

Herein, the terms "proximal" and "distal" refer to the ends of the electrosurgical instrument further from and closer to the treatment site, respectively. Thus, in use, the proximal end of the electrosurgical instrument is closer to a generator for providing the RF and/or microwave energy, whereas the distal end is closer to the treatment site, i.e. target tissue in the patient.

The term "conductive" is used herein to mean electrically conductive, unless the context dictates otherwise.

The term "longitudinal" used below refers to the direction along the length of the electrosurgical instrument, parallel to the axis of the coaxial transmission line. The term "inner" means radially closer to the centre (e.g. axis) of the instrument. The term "outer" means radially further from the centre (axis) of the instrument.

The term "electrosurgical" is used in relation an instrument, apparatus or tool which is used during surgery and which utilises microwave and/or radiofrequency electromagnetic (EM) energy.

BRIEF DESCRIPTION OF THE DRAWINGS

Examples of the invention are discussed below with reference to the accompanying drawings, in which.

DETAILED DESCRIPTION; FURTHER OPTIONS AND PREFERENCES

Figure 1:
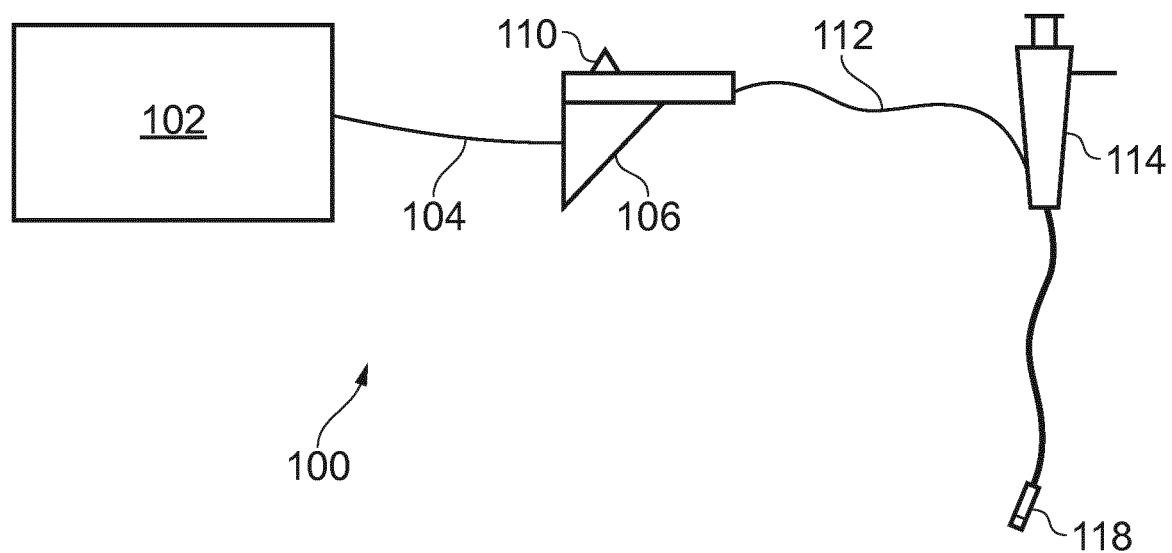
FIG. 1 is a schematic diagram of an electrosurgical system for tissue ablation that is an embodiment of the invention.

FIG. 1 is a schematic diagram of a complete electrosurgical system 100 that is capable of supplying microwave energy to the distal end of an invasive electrosurgical instrument. The system 100 comprises a generator 102 for controllably supplying microwave energy. A suitable generator for this purpose is described in wo 2012/076844, which is incorporated herein by reference. The generator may be arranged to monitor reflected signals received back from the instrument in order to determine an appropriate power level for delivery. For example, the generator may be arranged to calculate an impedance seen at the distal end of the instrument in order to determine an optimal delivery power level. The generator may be arranged to deliver power in a series of pulses which are modulated to match a patient's breathing cycle. This will allow for power delivery to occur when the lungs are deflated.

The generator 102 is connected to an interface joint 106 by an interface cable 104. If needed, the interface joint 106 can house an instrument control mechanism that is operable by sliding a trigger 110, e.g. to control longitudinal (back and forth) movement of one or more control wires or push rods (not shown). If there is a plurality of control wires, there may be multiple sliding triggers on the interface joint to provide full control. The function of the interface joint 106 is to combine the inputs from the generator 102 and instrument control mechanism into a single flexible shaft 112, which extends from the distal end of the interface joint 106. In other embodiments, other types of input may also be connected to the interface joint 106. For example, in some embodiments a fluid supply may be connected to the interface joint 106, so that fluid may be delivered to the instrument.

The flexible shaft 112 is insertable through the entire length of an instrument (working) channel of an endoscope 114.

The flexible shaft 112 has a distal assembly 118 (not drawn to scale in FIG. 1) that is shaped to pass through the instrument channel of the endoscope 114 and protrude (e.g. inside the patient) at the distal end of the endoscope's tube. The distal end assembly includes an active tip for delivering microwave energy into biological tissue. The tip configuration is discussed in more detail below.

The structure of the distal assembly 118 may be arranged to have a maximum outer diameter suitable for passing through the working channel. Typically, the diameter of a working channel in a surgical scoping device such as an endoscope is less than 4.0 mm, e.g. any one of 2.0 mm, 2.8 mm, 3.2 mm, 3.7 mm, 3.8 mm. The length of the flexible shaft 112 can be equal to or greater than 0.3 m, e.g. 2 m or more. In other examples, the distal assembly 118 may be mounted at the distal end of the flexible shaft 112 after the shaft has been inserted through the working channel (and before the instrument cord is introduced into the patient). Alternatively, the flexible shaft 112 can be inserted into the working channel from the distal end before making its proximal connections. In these arrangements, the distal end assembly 118 can be permitted to have dimensions greater than the working channel of the surgical scoping device 114.

The system described above is one way of introducing the instrument into a patient's body. Other techniques are possible. For example, the instrument may also be inserted using a catheter.

Figure 2:
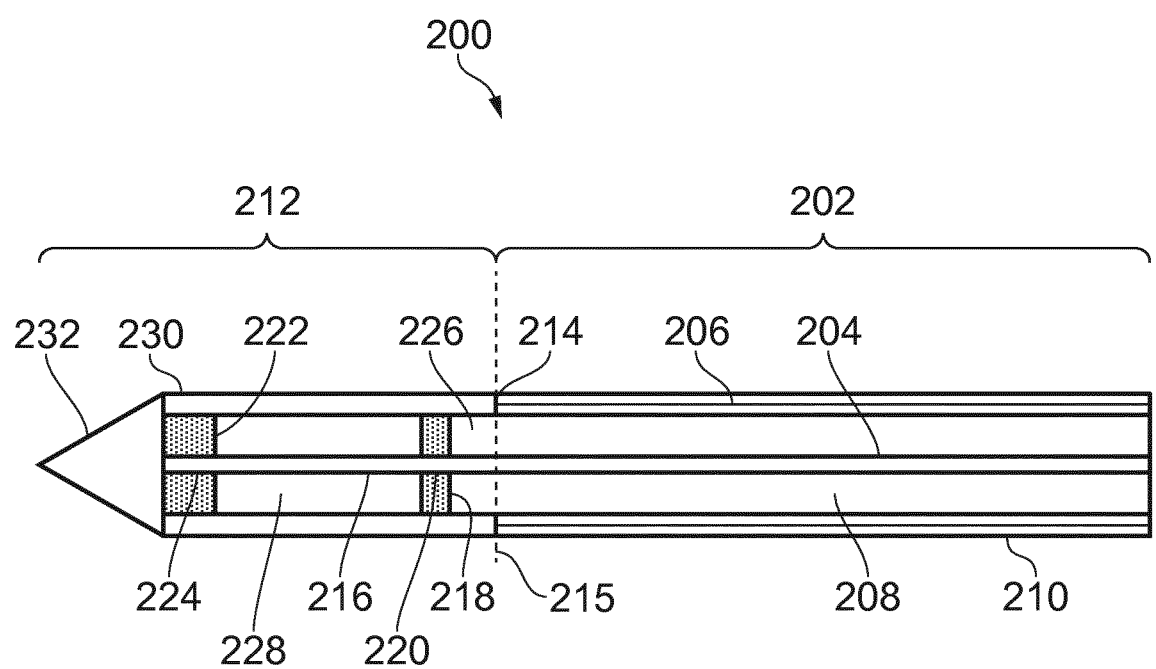
FIG. 2 is a schematic cross-sectional side view of an electrosurgical instrument that is an embodiment of the invention.

FIG. 2 shows a cross-sectional side view of an electrosurgical instrument 200 that is an embodiment of the invention. The distal end of the electrosurgical instrument may correspond, for example, to the distal assembly 118 discussed above. The electrosurgical instrument 200 includes a coaxial feed cable 202 that is connectable at its proximal end to a generator (such as generator 102) in order to convey microwave energy. The coaxial feed cable 202 may be the interface cable 104 discussed above, which passes through the flexible shaft 112. The coaxial feed cable 202 comprises an inner conductor 204 and an outer conductor 206 which are separated by a dielectric material 208. The coaxial feed cable 202 is preferably low loss for microwave energy. A choke (not shown) may be provided on the coaxial feed cable 204 to inhibit back propagation of microwave energy reflected from the distal end and therefore limit backward heating along the device. The coaxial feed cable 202 further includes a flexible outer sheath 210 disposed around the outer conductor 206 to protect the coaxial feed cable 204. The outer sheath 210 may be made of an insulating material to electrically isolate the outer conductor 206 from its surroundings. The outer sheath 210 may be made of, or coated with, a non-stick material such as PTFE to prevent tissue from sticking to the instrument.

A radiating tip 212 is formed at the distal end 214 of the coaxial feed cable 202. The dashed line 215 in FIG. 2 illustrates an interface between the coaxial feed cable 202 and the radiating tip 212. The radiating tip 212 is arranged to receive microwave energy conveyed by the coaxial feed cable 202, and deliver the energy into biological tissue. The outer conductor 206 of the coaxial feed cable 202 terminates at the distal end 214 of the coaxial feed cable 202, i.e. the outer conductor 206 does not extend into the radiating tip 212. The radiating tip 212 includes a distal portion 216 of the inner conductor 204 which extends beyond the distal end of the coaxial feed cable 202. In particular, the distal portion 216 of the inner conductor 204 extends beyond a distal end of the outer conductor 206.

A proximal tuning element 218 made of a conductive material (e.g. metal) is electrically connected to the distal portion 216 of the inner conductor 204 near a proximal end of the radiating tip 212. The proximal tuning element 218 has a cylindrical shape, and includes a channel 220 through which the distal portion 216 of the inner conductor 204 passes. A diameter of the channel 220 is substantially the same as an outer diameter of the inner conductor 204, such that the inner conductor 204 is in contact with the proximal tuning element 218 inside the channel 220. The proximal tuning element 218 may be further secured to the inner conductor 204, e.g. using a conductive adhesive (e.g. conductive epoxy) or by soldering or welding. The proximal tuning element 218 is centred on the inner conductor 204. In other words, a central axis of the cylindrical proximal tuning element 218 is collinear with the longitudinal axis of the inner conductor 204. In this manner, the proximal tuning element 218 is disposed around the distal portion 216 of the inner conductor 204 in a manner that is symmetrical about the longitudinal axis of the inner conductor 204.

A distal tuning element 222 made of a conductive material (e.g. metal) is electrically connected to the distal portion 216 of the inner conductor 204 near a distal end of the radiating tip 212. Thus, the distal tuning element 222 is located further along the inner conductor 204 than the proximal tuning element 218. The distal tuning element 222 is spaced apart from the proximal tuning element by a length of the distal portion 216 of the inner conductor 204. Like the proximal tuning element 218, the distal tuning element has a cylindrical shape and includes a channel 224. As can be seen in FIG. 2, the distal portion 216 of the inner conductor 204 extends into the channel 224. The distal portion 216 of the inner conductor 204 terminates at a distal end of the channel 224, i.e. it does not protrude beyond the distal tuning element 222. In this manner, a distal end of the inner conductor 204 lies flush with a distal face of the distal tuning element 222. A diameter of the channel 224 is substantially the same as the outer diameter of the inner conductor 204, such that the inner conductor 204 is in contact with the distal tuning element 222 inside the channel 224. The distal tuning element 222 may be further secured to the inner conductor 204, e.g. using a conductive adhesive (e.g. conductive epoxy) or by soldering or welding. Like the proximal tuning element 218, the distal tuning element 222 is mounted so that it is centred on the inner conductor 204.

Both the proximal tuning element 218 and the distal tuning element 222 have the same outer diameter. The outer diameter of the proximal tuning element 218 and the distal tuning element 222 may be slightly less than the outer diameter of the electrosurgical instrument 200. In the example shown, the distal tuning element 222 is longer than the proximal tuning element 218 in the longitudinal direction of the instrument. In other words, the length of inner conductor 204 in channel 224 in the distal tuning element 222 is greater than the length of inner conductor 204 in channel 220 in the proximal tuning element 218. For example, the distal tuning element 222 may be approximately twice as long as the proximal tuning element 218. By making the distal tuning element 222 longer than the proximal tuning element 218, it is possible to concentrate microwave emission around the distal end of the radiating tip 212.

A distal portion 226 of the dielectric material 208 extends beyond the distal end 214 of the coaxial feed cable 202 into the radiating tip 212. The distal portion 226 of the dielectric material 208 acts as a spacer between the proximal tuning element 218 and the distal end 214 of the coaxial feed cable 202. In some embodiments (not shown), the dielectric material 208 may terminate at the distal end 214 of the coaxial feed cable 202, and a separate spacer may be provided between the distal end 214 of the coaxial feed cable 202 and the proximal tuning element 218. A dielectric spacer 228 is provided in the radiating tip 212 between the proximal tuning element 218 and the distal tuning element 222. The dielectric spacer 228 is a cylindrical piece of dielectric material, having a central channel extending therethrough. Thus, the dielectric spacer 228 may be a tube of dielectric material. The distal portion 214 of the inner conductor 204 extends through the channel in the dielectric spacer 228. A proximal face of the dielectric spacer 228 is in contact with the proximal tuning element 218, and a distal face of the dielectric spacer 228 is in contact with the distal tuning element 222. The dielectric spacer 228 has approximately the same outer diameter as the proximal and distal tuning elements 218, 222.

A protective sheath 230 is provided on the outside of the radiating tip 212. The protective sheath 230 covers the dielectric spacer 228 and the proximal and distal tuning elements 218, 222 to form an outer surface of the radiating tip 212. The protective sheath 230 may be a tube made of an insulating material. The protective sheath 230 may serve to insulate the radiating tip 212 and protect it from the environment. The protective sheath 230 may be made of or coated with a non-stick material (e.g. PTFE) to prevent tissue from sticking to it. An outer diameter of the protective sheath 230 is substantially the same as the outer diameter of the coaxial feed cable 202, so that the instrument has a smooth outer surface, i.e. the radiating tip 212 has an outer surface that is flush with an outer surface of the coaxial feed cable 202 at the interface 215. In some embodiments (not shown) the protective sheath 230 may be a continuation of the outer sheath 210 of the coaxial feed cable 202. Together, the distal portion 226 of the dielectric material 208, the dielectric spacer 228 and the protective sheath 230 form a dielectric body of the radiating tip 212.

The radiating tip 212 further includes a distal tip 232 located at its distal end. The distal tip 232 may be pointed in order to facilitate insertion of the radiating tip 212 into target tissue. However, in other embodiments (not shown), the distal tip may be rounded or flat. The distal tip 232 may be made of a dielectric material, e.g. the same as dielectric material 208. In some embodiments, the material of the distal tip 232 may be selected to improve impedance matching with target tissue, in order to improve the efficiency with which the EM energy is delivered to the target tissue. The distal tip 232 may be made of, or covered with a non-stick material (e.g. PTFE) to prevent tissue from sticking to it.

The following are example dimensions of electrosurgical instrument 200:
- distance from the interface 215 to the distal end of the distal portion 216 of the inner conductor 204: 5.75 mm;
- outer diameter of proximal tuning element 218 and distal tuning element 222: 1.5 mm;
- length of proximal tuning element 218: 0.5 mm;
- length of distal tuning element 222: 1.0 mm;
- spacing between proximal tuning element 218 and distal tuning element 222: 3.75 mm;
- spacing between the proximal tuning element 218 and the interface 215: 0.5 mm; and
- outer diameter of electrosurgical instrument 200: 1.85 mm.

The radiating tip 212 may act as a microwave monopole antenna when microwave energy is conveyed to the radiating tip 212. In particular, microwave energy may be radiated from the distal portion 216 of the inner conductor 202, so that microwave energy can be delivered into surrounding biological tissue. The proximal and distal tuning elements 218, 222 act to shape the radiation profile of the radiating tip 212, and improve impedance matching between the instrument and surrounding target tissue, as discussed below.

Figure 3:
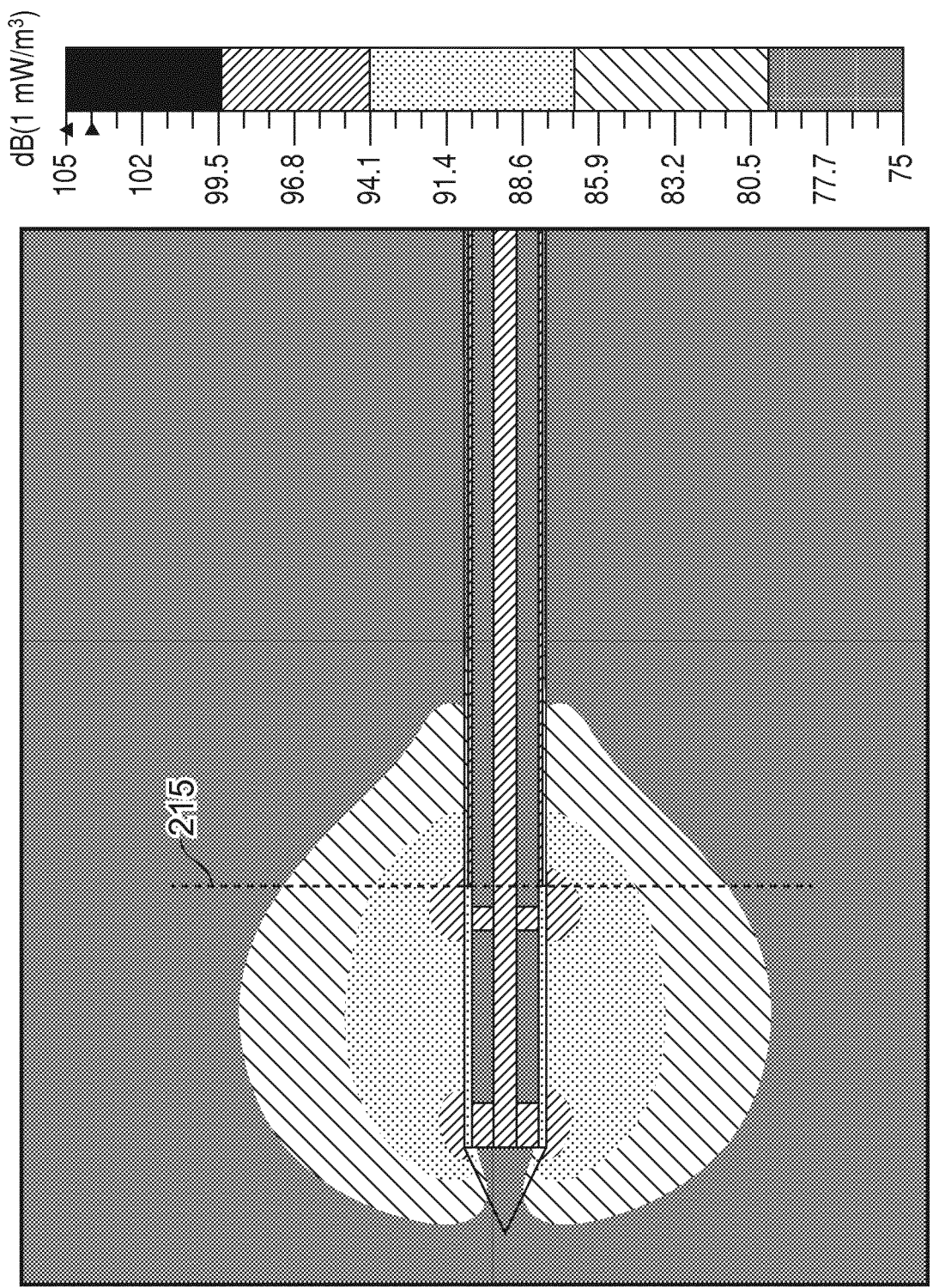
FIG. 3 is a diagram showing a simulated radiation profile for an electrosurgical instrument that is an embodiment of the invention.

FIG. 3 shows a simulated microwave radiation profile in target tissue for the electrosurgical instrument 200 illustrated in FIG. 2. The radiation profile was simulated for a microwave frequency of 5.8 GHZ, using finite element analysis software. The radiation profile is indicative of the resultant shape of tissue ablated by the microwave energy. As can be seen in FIG. 3, the radiation profile is concentrated around the radiating tip, and defines an approximately spherical region. In this manner, tissue may be ablated in an approximately spherical region around the radiating tip. The interface 215 between the radiating tip and coaxial feed cable is shown to aid visualisation of the location and shape of the field relative to the tip of the instrument.

Figure 4:
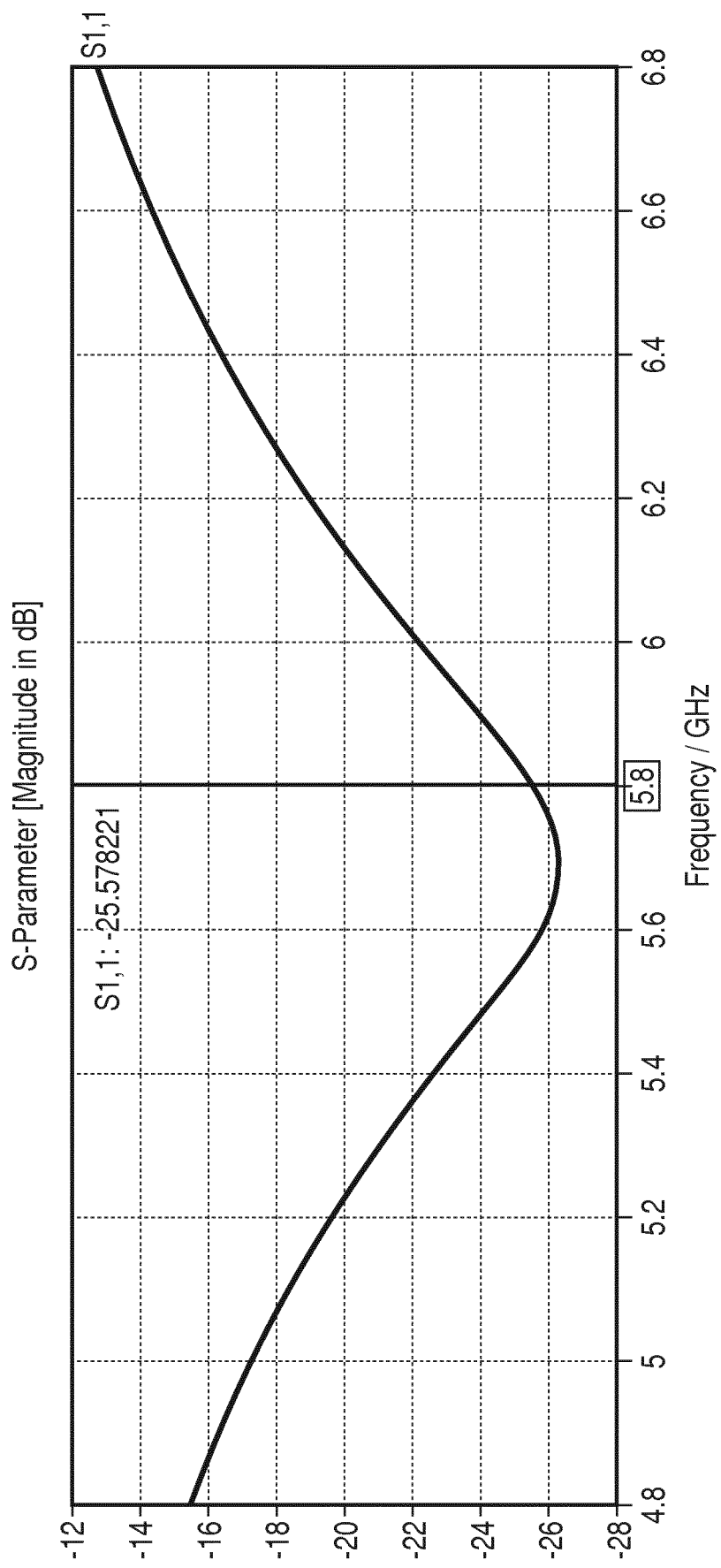
FIG. 4 is a plot of the simulated return loss for an electrosurgical instrument that is an embodiment of the invention.

FIG. 4 shows a simulated plot of the S-parameter (also known as the input reflection coefficient $S_{11}$, or "return loss") against frequency of the microwave energy for the electrosurgical instrument 200. As well known in the technical field, the S-parameter is a measure of the return loss of microwave energy due to impedance mismatch, and as such the S-parameter is indicative of the degree of impedance mismatch between the target tissue and the radiating tip. The S-parameter can be defined by the equation $P_I = S P_R$, where $P_I$ is the outgoing power in the instrument towards the tissue, $P_R$ is the power reflected back from the tissue, and S is the S-parameter. As shown in FIG. 4, the S-parameter has a value of −25.58 dB at 5.8 GHz, meaning that very little microwave energy is reflected back from the tissue at this frequency. This indicates a good impedance match at the operating frequency of 5.8 GHZ, and that microwave energy is efficiently delivered from the radiating tip into the tissue at this frequency.

Figure 5:
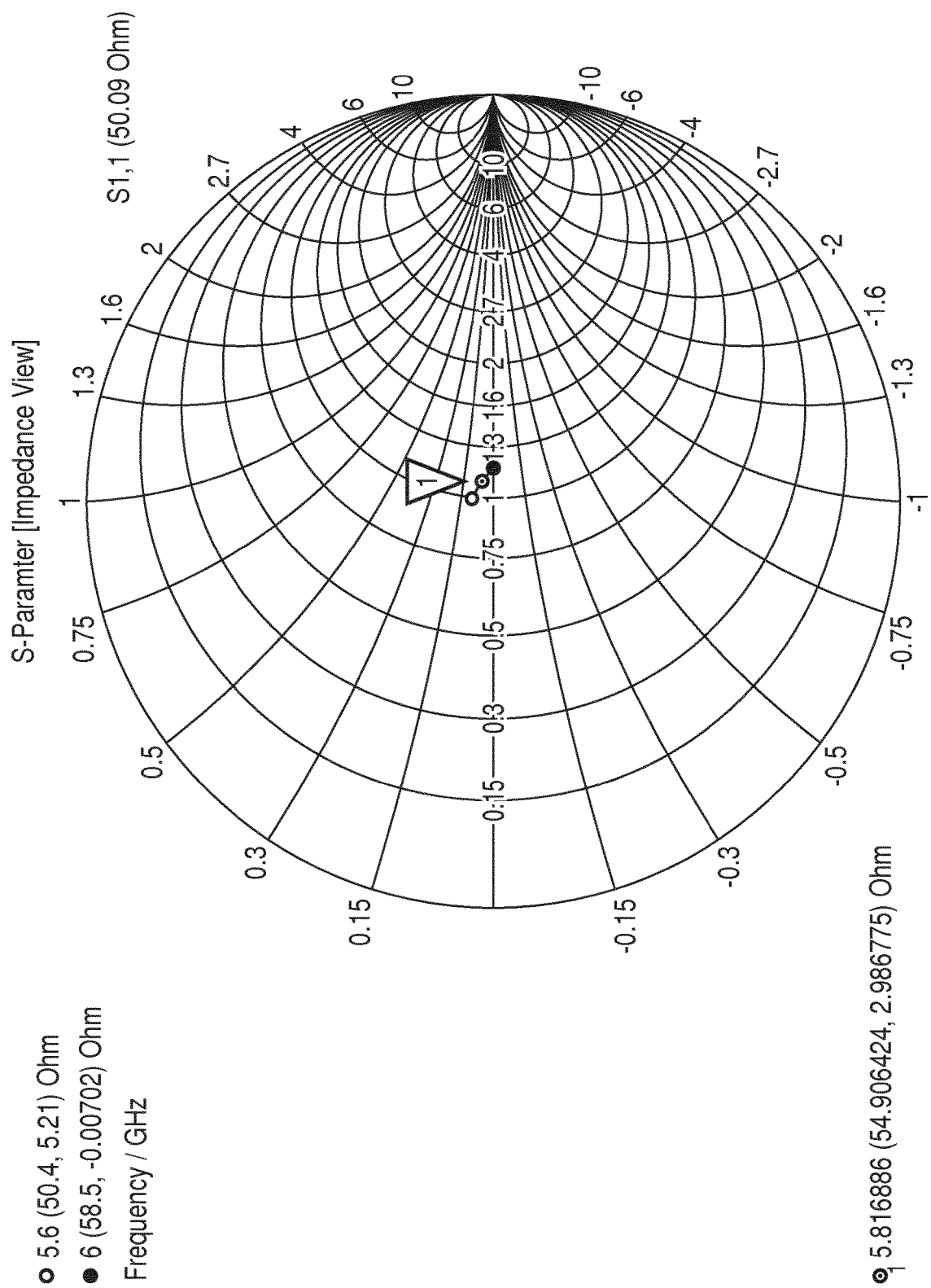
FIG. 5 shows a Smith chart having plotted thereon various parameters calculated for an electrosurgical instrument that is an embodiment of the invention.

FIG. 5 shows a simulated impedance Smith chart for the electrosurgical instrument 200. The Smith chart was simulated for a reference plane locating at the interface 215 between the distal end of the coaxial feed cable and the radiating tip. As well known in the technical field, the Smith chart is a graphical representation of the S-parameter (reflection coefficient) in the complex plane. The S-parameter may be defined by the following equation:

$$S = \frac{z-1}{z+1}$$

where $z = Z/Z_0$, Z being the impedance of the radiating tip in contact with target tissue, and $Z_0$ being a normalisation factor. In the present case, a normalisation factor of 50 Ohm was used, as this is a typical characteristic impedance of the coaxial feed cable, the interface cable (e.g. interface cable 104) and the electrosurgical generator (e.g. generator 102). In FIG. 5, the marker (labelled "1") indicates the value of the S-parameter at 5.8 GHz. As can be seen, the value of the S-parameter is near the unity mark (i.e. the point where z=1). This shows a good impedance matching between the generator, interface cable, coaxial feed cable and the antenna in contact with the target tissue. In other words, microwave energy may be efficiently delivered from the radiating tip into target tissue. The value of the impedance Z at 5.8 GHz is indicated in the legend of FIG. 5, and is (54.9+12.9) Ohm. The full circle and the empty circle next to the marker in FIG. 5 indicate points at 6 GHz and 5.6 GHZ, respectively. The value of the impedance Z for these points is shown in the legend of FIG. 5.

Figure 6:
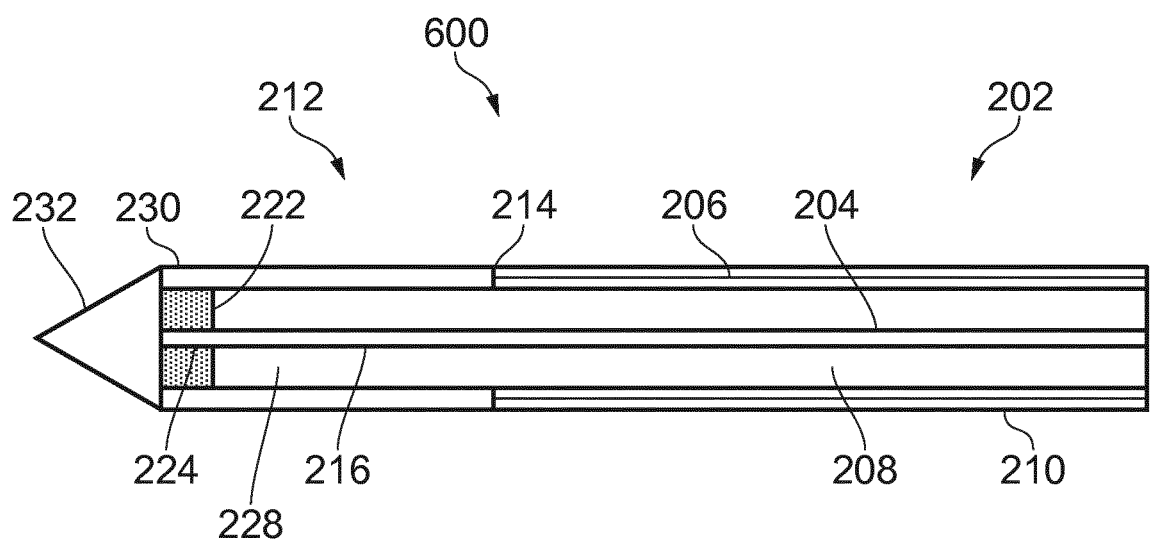
FIG. 6 is a schematic cross-sectional side view of an electrosurgical instrument that is a comparative example.
Figure 7:
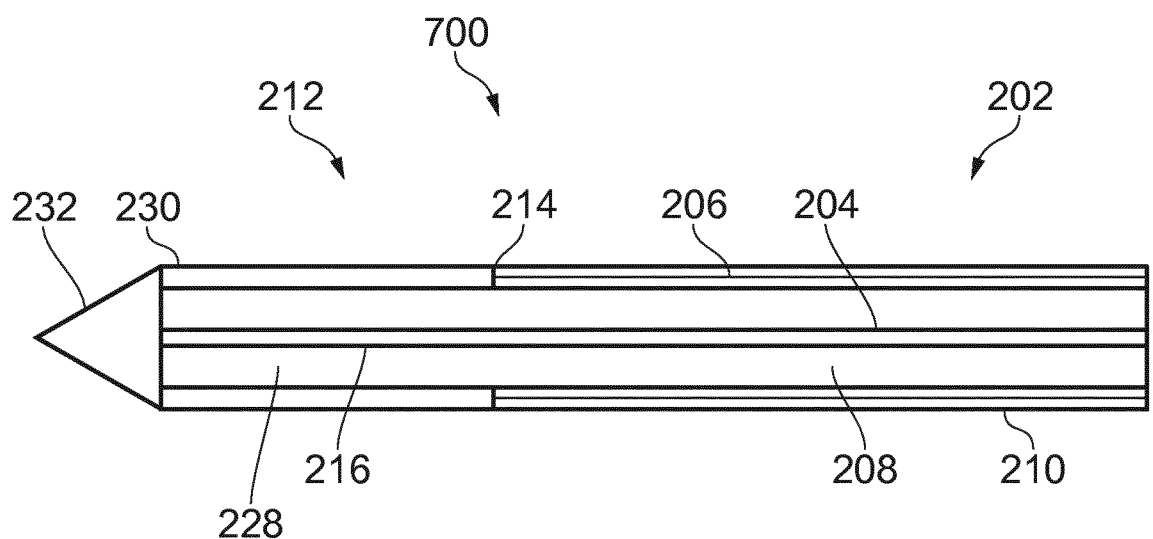
FIG. 7 is a schematic cross-sectional side view of an electrosurgical instrument that is another comparative example.

We now turn to comparative examples shown in FIGS. 6-13, to illustrate the effects of the proximal and distal tuning elements in more detail. FIG. 6 shows an electrosurgical instrument 600 which is a first comparative example, and FIG. 7 shows an electrosurgical instrument 700 which is a second comparative example. Electrosurgical instrument 600 is similar to electrosurgical instrument 200, except that electrosurgical instrument 600 does not include a proximal tuning element. All other features of electrosurgical instrument 600 (including the distal tuning element) are the same as for electrosurgical instrument 200. Electrosurgical instrument 700 is similar to electrosurgical instrument 200, except that electrosurgical instrument 700 does not include a proximal tuning element or a distal tuning element (i.e. both tuning elements are absent). All other features of electrosurgical instrument 700 are the same as for electrosurgical instrument 200. Reference numerals used in FIG. 2 are used in FIGS. 6 and 7 to indicate features corresponding to those discussed above in relation to FIG. 2.

Figure 8:
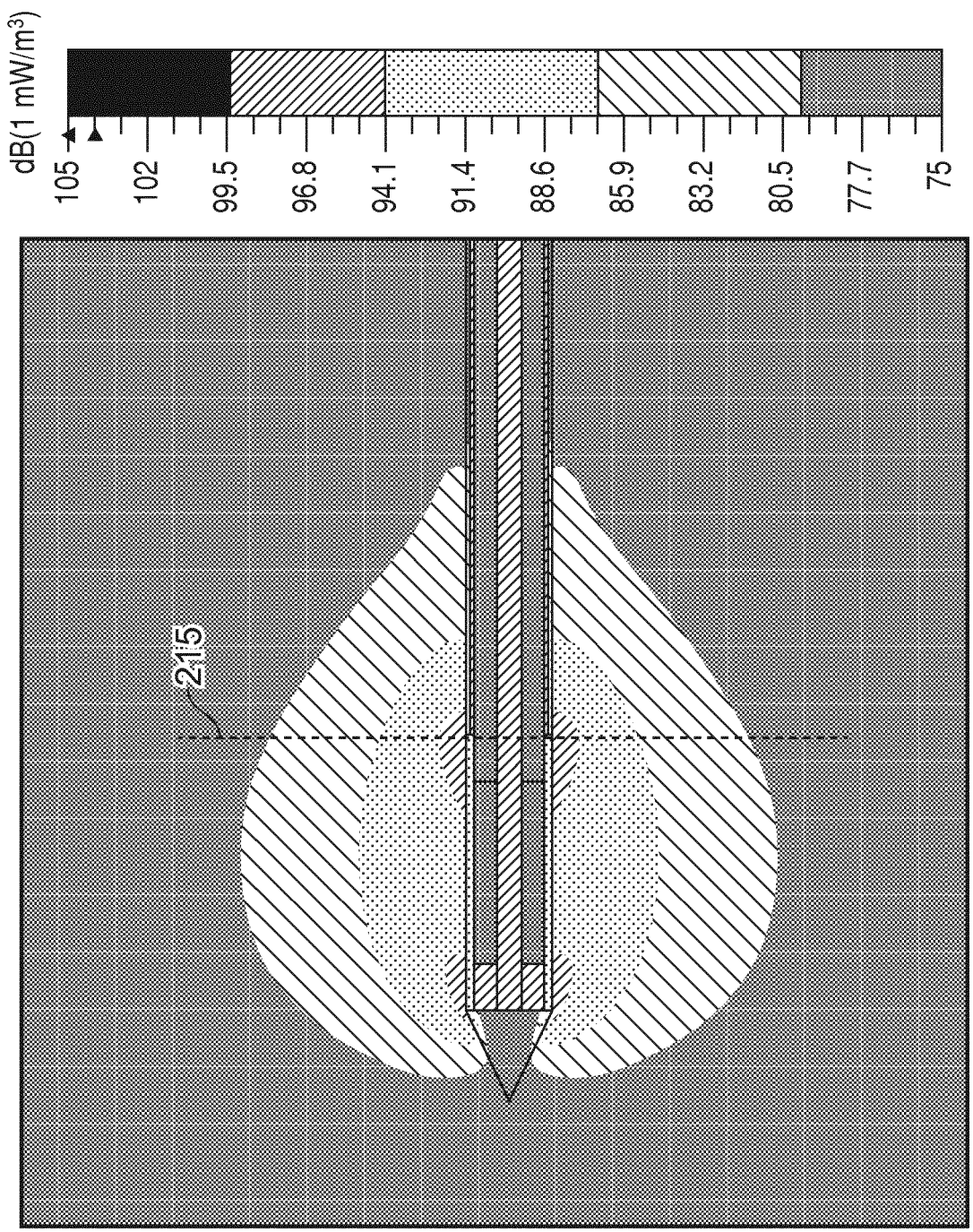
FIG. 8 is a diagram showing a simulated radiation profile for the electrosurgical instrument of FIG. 6.

FIG. 8 shows a simulated microwave radiation profile in target tissue for the electrosurgical instrument 600 illustrated in FIG. 6. The radiation profile was simulated for a microwave frequency of 5.8 GHZ, using finite element analysis software. Except for the lack of a proximal tuning element, the dimensions of electrosurgical instrument 600 used for the calculation were the same as those used to calculate the radiation profile of electrosurgical instrument 200 shown in FIG. 3. As can be seen by comparing FIGS. 3 and 8, the radiation profile of electrosurgical instrument 600 is less spherical than the radiation profile of electrosurgical instrument 200. In particular, the radiation profile of electrosurgical instrument 600 includes a tail which extends back down a longer portion of the coaxial feed cable than a tail on the radiation profile of electrosurgical instrument 200. Thus, the proximal tuning element acts to make the radiation profile more spherical, and reduce the tail which extends back down the coaxial feed cable. Such a tail may be undesirable, as it may cause heating in the coaxial feed cable and/or cause ablation of tissue which is outside of a target zone.

Figure 9:
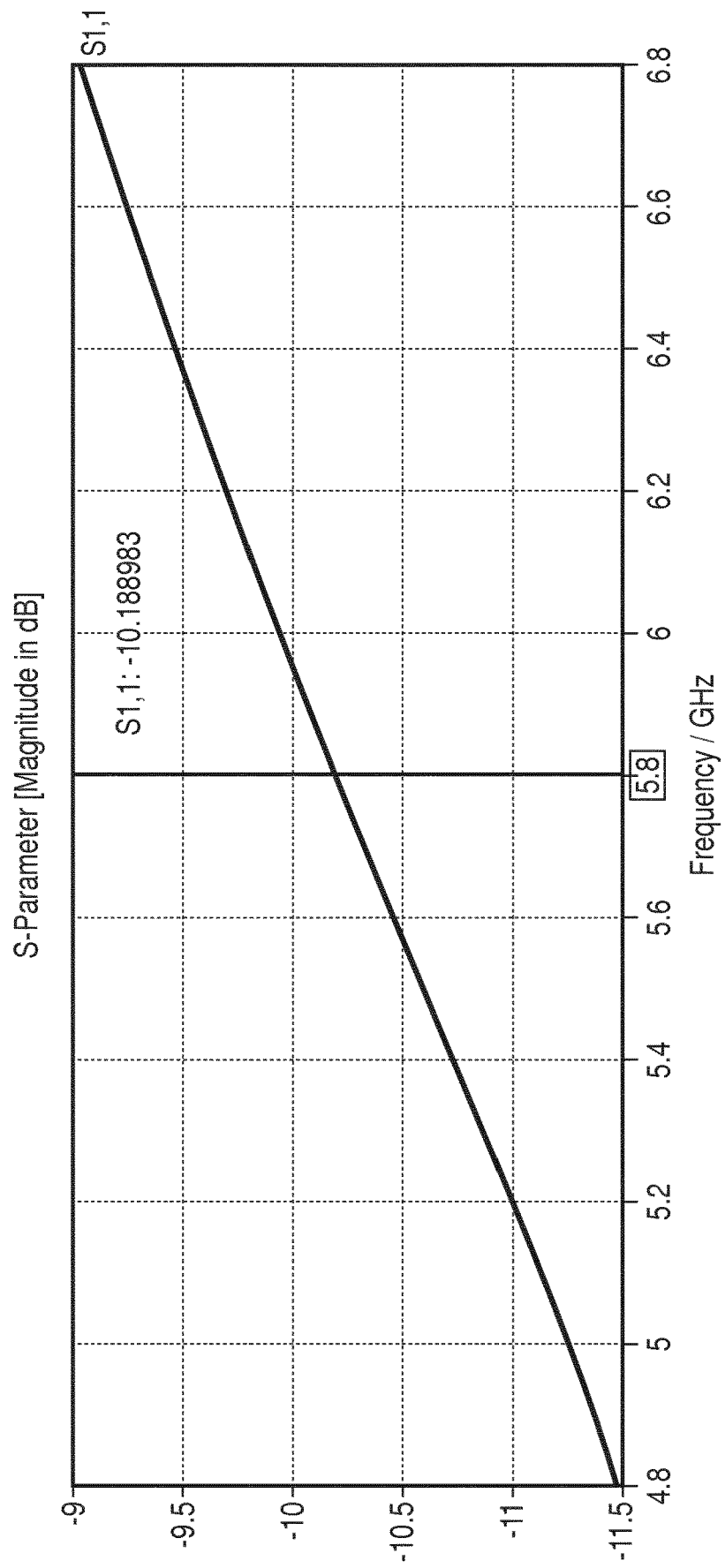
FIG. 9 is a plot of the simulated return loss for the electrosurgical instrument of FIG. 6.

FIG. 9 shows a simulated plot of the S-parameter against frequency of the microwave energy for the electrosurgical instrument 600. The plot in FIG. 9 was calculated in the same way as the plot in FIG. 4 for electrosurgical instrument 200. As shown in FIG. 9, the S-parameter has a value of −10.18 dB at 5.8 GHz. This indicates a much greater return loss compared to electrosurgical instrument 200, where the S-parameter was found to have a value of −25.58 dB. The proximal tuning element therefore serves to improve impedance matching. Microwave energy may therefore be more efficiently delivered into target tissue with electrosurgical instrument 200 than with electrosurgical instrument 600.

Figure 10:
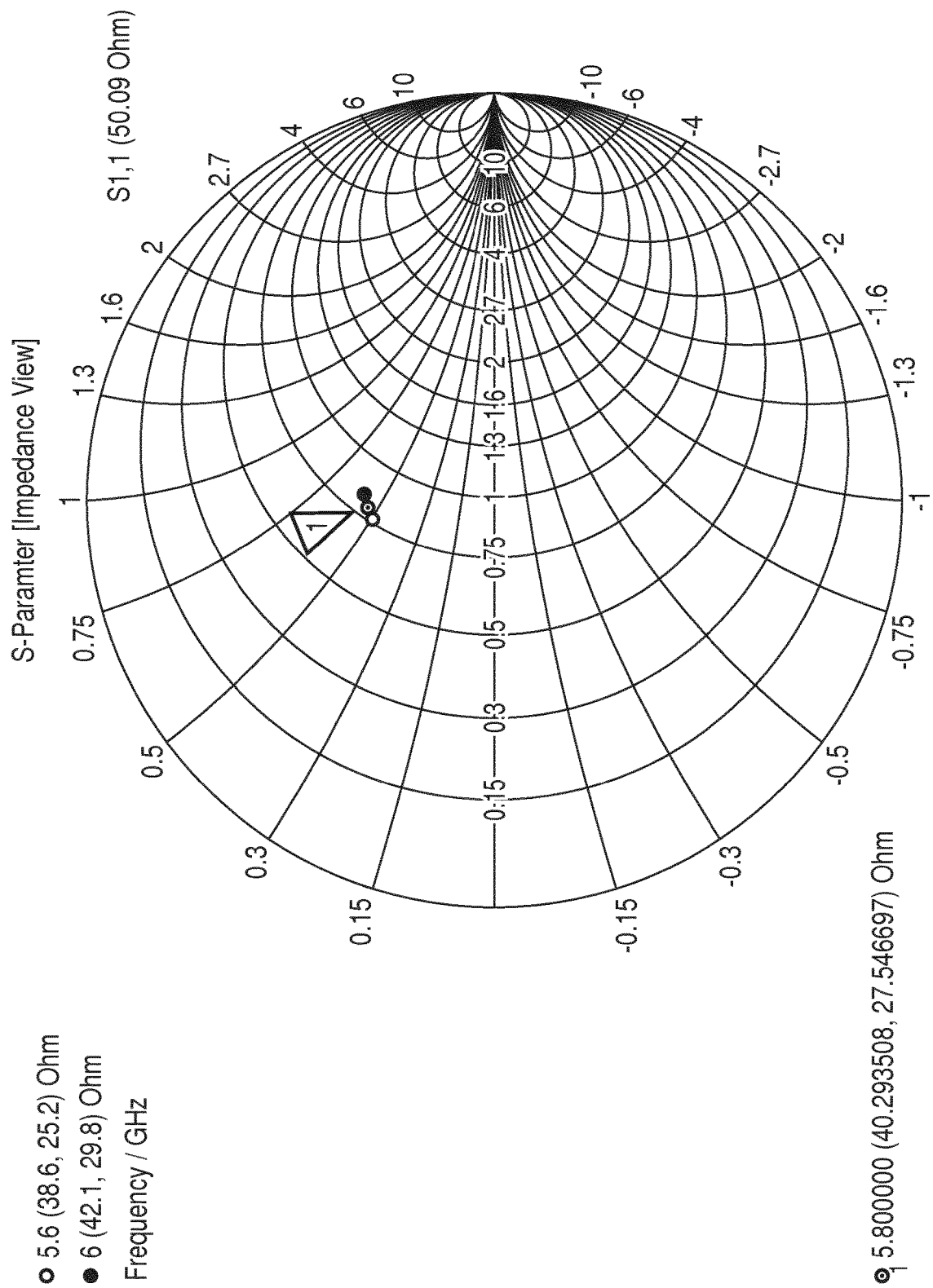
FIG. 10 shows a Smith chart having plotted thereon various parameters calculated for the electrosurgical instrument of FIG. 6.

FIG. 10 shows a simulated impedance Smith chart for electrosurgical instrument 600. This was calculated in the same way as the Smith chart for electrosurgical instrument 200 shown in FIG. 5. The marker in FIG. 10 (labelled "1") indicates the value of the S-parameter at 5.8 GHz. As can be seen, the marker is further away from the unity mark compared to FIG. 5. This shows a less good impedance match between the generator, interface cable, coaxial feed cable and the antenna in contact with the target tissue, compared to electrosurgical instrument 200. By comparing FIGS. 5 and 10, it can be seen that the effect of adding the proximal tuning element is to move the marker downwards closer to the unity mark. This indicates that the proximal tuning element introduces an additional capacitance into the system. The shift of the marker closer to the unity mark in FIG. 5 may also be related to the phase shift associated with the distance between the distal end of the coaxial feed cable and the proximal end of the proximal tuning element. The value of the impedance Z of electrosurgical instrument 600 at 5.8 GHz is indicated in the legend of FIG. 10, and is (40.2+127.5) Ohm. The full circle and the empty circle next to the marker in FIG. 10 indicate points at 6 GHz and 5.6 GHz, respectively. The value of the impedance Z for these points is shown in the legend of FIG. 10.

Figure 11:
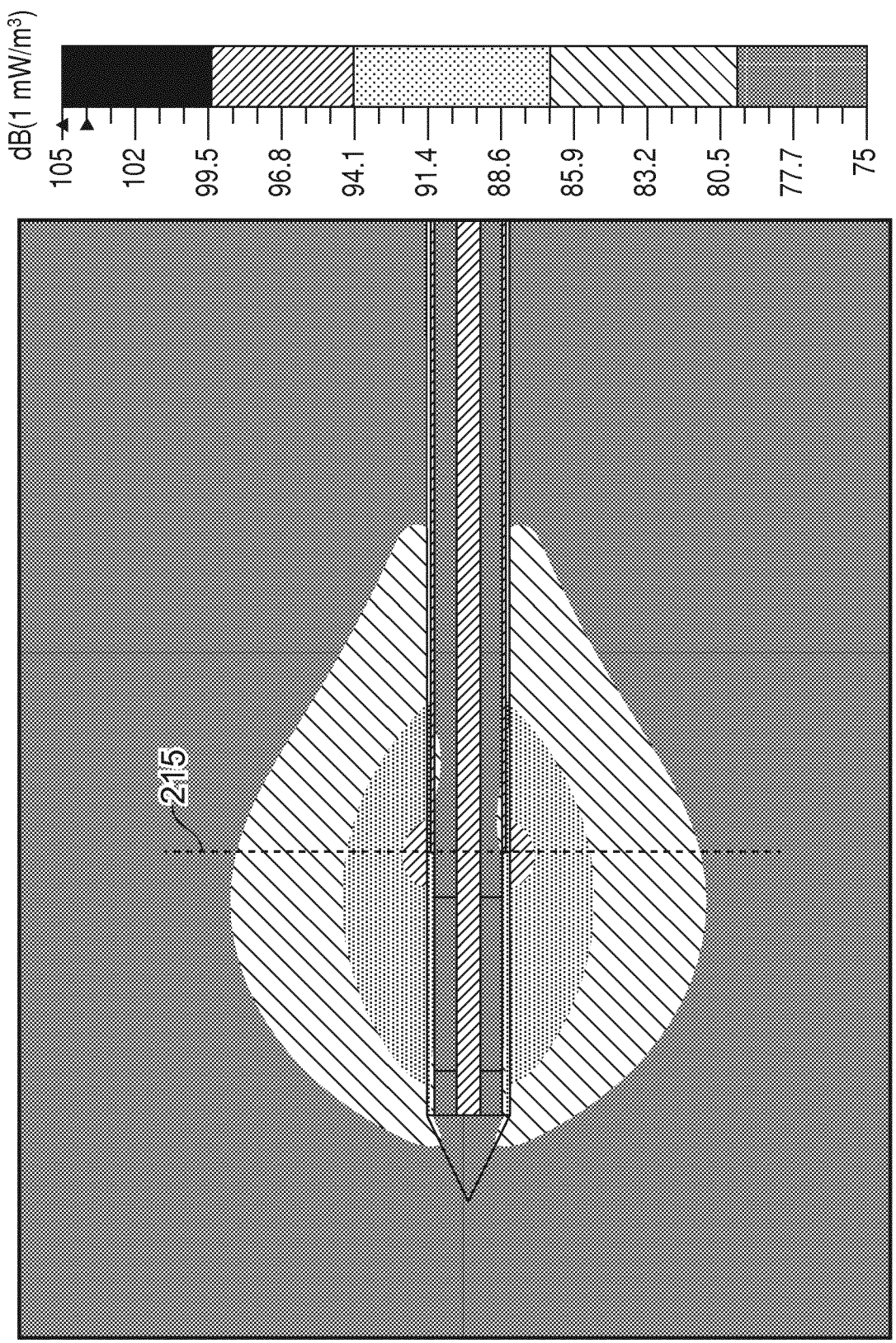
FIG. 11 is a diagram showing a simulated radiation profile for the electrosurgical instrument of FIG. 7.

FIG. 11 shows a simulated microwave radiation profile in target tissue for the electrosurgical instrument 700 illustrated in FIG. 7. The radiation profile was simulated for a microwave frequency of 5.8 GHZ, using finite element analysis software. Except for the lack of a proximal and distal tuning elements, the dimensions of electrosurgical instrument 700 used for the calculation were the same as those used to calculate the radiation profile of electrosurgical instrument 200 shown in FIG. 3. As can be seen by comparing FIGS. 3, 8 and 11, the radiation profile of electrosurgical instrument 700 is even less spherical and more elongate than the radiation profile of electrosurgical instrument 600. In particular, the radiation profile of electrosurgical instrument 700 is less concentrated around the distal tip of the instrument, and has a longer tail extending back down the coaxial feed cable. Thus, the distal tuning element acts to make the radiation profile more spherical, and reduce the tail which extends back down the coaxial feed cable.

Figure 12:
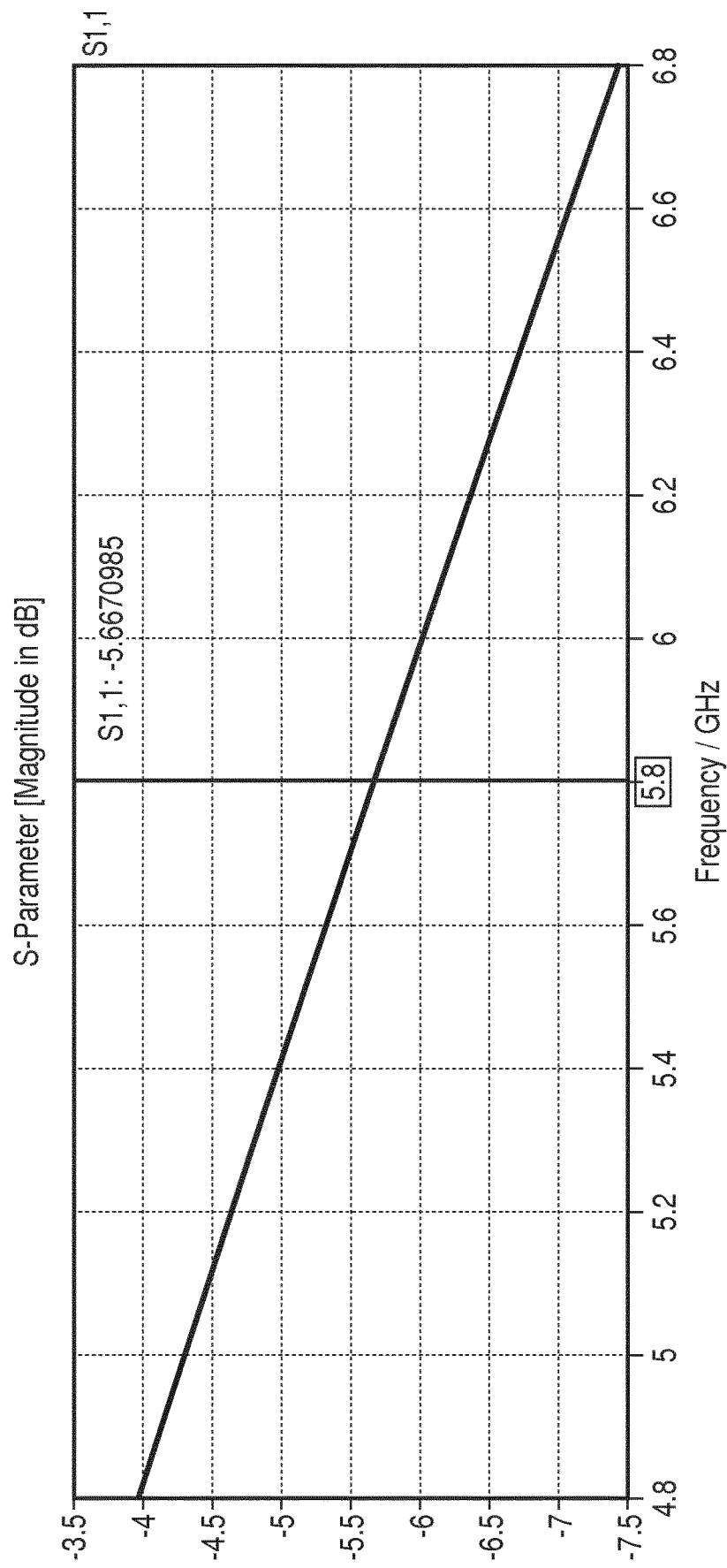
FIG. 12 is a plot of the simulated return loss for the electrosurgical instrument of FIG. 7.

FIG. 12 shows a simulated plot of the S-parameter against frequency of the microwave energy for the electrosurgical instrument 700. The plot in FIG. 12 was calculated in the same way as the plot in FIG. 4 for electrosurgical instrument 200. As shown in FIG. 12, the S-parameter has a value of −5.66 dB at 5.8 GHz. This indicates a much greater return loss compared to electrosurgical instruments 200 and 600, where the S-parameter was found to have a value of −25.58 dB and −10.18 dB, respectively. The distal tuning element therefore serves to improve impedance matching.

Figure 13:
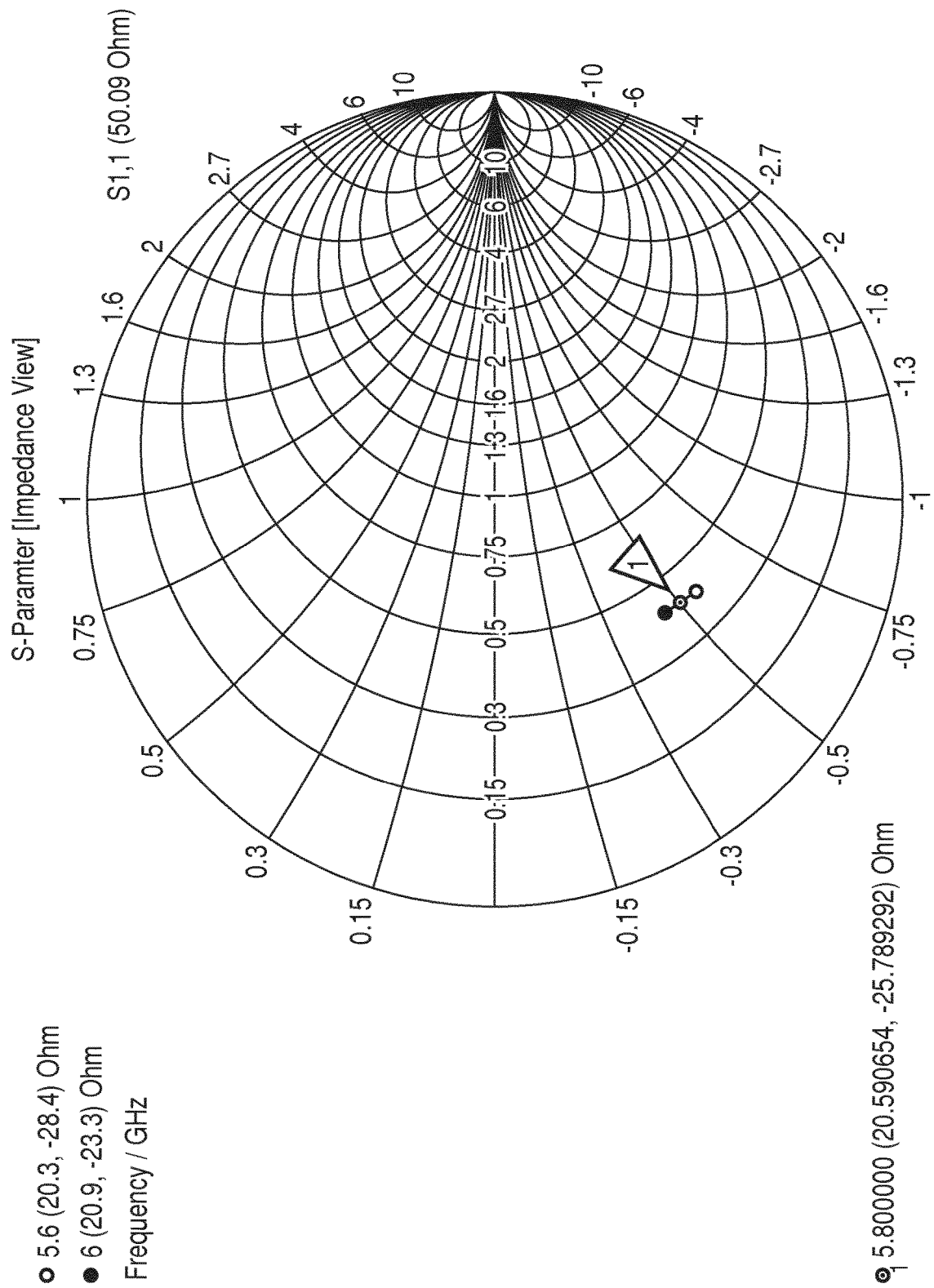
FIG. 13 shows a Smith chart calculated for the electrosurgical instrument of FIG. 7.

FIG. 13 shows a simulated impedance Smith chart for electrosurgical instrument 700. This was calculated in the same way as the Smith chart for electrosurgical instrument 200 shown in FIG. 5. The marker in FIG. 13 (labelled "1") indicates the value of the S-parameter at 5.8 GHz. As can be seen, the marker is further away from the unity mark compared to FIG. 5. This shows a less good impedance match between the generator, interface cable, coaxial feed cable and the antenna in contact with the target tissue, compared to electrosurgical instrument 200. The marker in FIG. 13 is also further away from the unity mark compared to FIG. 10, indicating a less good impedance match. The value of the impedance Z of electrosurgical instrument 700 at 5.8 GHz is indicated in the legend of FIG. 13, and is (20.5-125.7) Ohm. The full circle and the empty circle next to the marker in FIG. 13 indicate points at 6 GHz and 5.6 GHz, respectively. The value of the impedance Z for these points is shown in the legend of FIG. 13.

Figure 14:
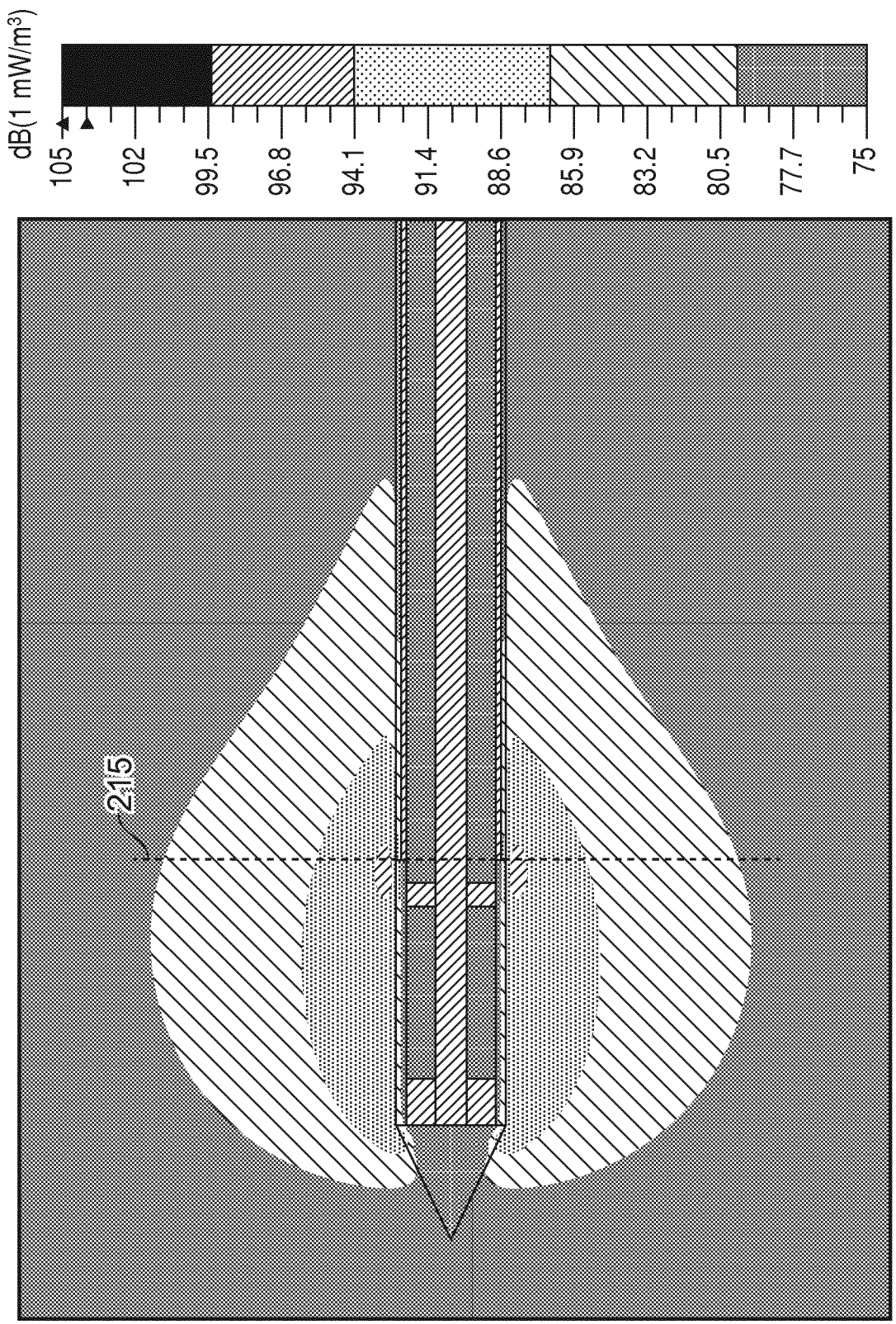
FIG. 14 is a diagram showing a simulated radiation profile for an electrosurgical instrument that is an embodiment of the invention.

In summary, the comparative examples show that the presence of both the proximal and distal tuning elements in the radiating tip serves to enhance the radiation profile of the radiating tip, by making the radiation profile more spherical and reducing the tail that extends back down the coaxial feed cable. The comparative examples also show that the proximal and distal tuning elements serve to improve impedance matching, which may improve the efficiency with which microwave energy can be delivered into target tissue. The inventors have found that, as the outer diameter of the electrosurgical instrument is increased, the tail in the radiation profile that extends back down the coaxial feed cable increases. This is illustrated in FIG. 14, which shows a simulated microwave radiation profile in target tissue for an electrosurgical instrument according to an embodiment of the invention. The electrosurgical instrument of FIG. 14 is similar to electrosurgical instrument 200 described above, except that it has an outer diameter of 2.6 mm (whereas electrosurgical instrument 200 has an outer diameter of 1.85 mm). The radiation profile was simulated for a microwave frequency of 5.8 GHz, using finite element analysis software. The dashed line indicated by numeral 215 in FIG. 14 shows the position of the interface between the coaxial feed cable and the radiating tip. As can be seen by comparing FIG. 14 with the radiation profile for electrosurgical instrument 200, the tail that extends back down the coaxial feed cable is larger for the electrosurgical instrument of FIG. 14, i.e. the electrosurgical instrument having the larger outer diameter.

Figure 15:
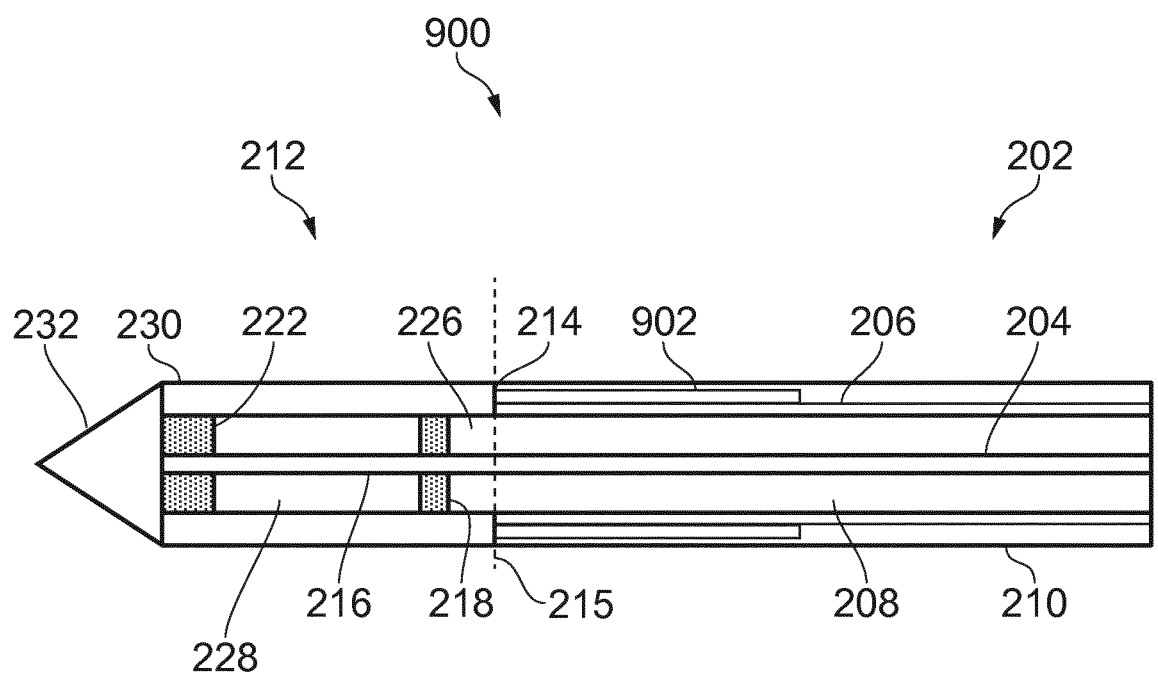
FIG. 15 is a schematic cross-sectional side view of an electrosurgical instrument that is an embodiment of the invention.

The inventors have found that the tail in the radiation profile may be suppressed by including a field shaping element at a distal end of the coaxial feed cable. FIG. 15 shows a cross-sectional side view of an electrosurgical instrument 900 that is an embodiment of the invention. The electrosurgical instrument 900 is similar to electrosurgical instrument 200 discussed above, except that it includes a field shaping element 902, and its outer diameter is 2.6 mm. Reference numerals used in FIG. 2 are used in FIG. 15 to indicate features corresponding to those discussed above in relation to FIG. 2.

The field shaping element 902 is an annular sleeve of conductive material disposed around an outer surface of the outer conductor 206. The field shaping element 902 is located at the distal end of the coaxial feed cable 202, and extends from the interface 215 along a length of the coaxial feed cable 202. The length of the field shaping element 902 corresponds to a quarter wavelength of the microwave energy to be conveyed by the coaxial feed cable 202. In the case where microwave energy is at 5.8 GHz, the length of the field shaping element 902 may be approximately 9 mm. An inner surface of the field shaping element 902 is in contact with the outer surface of the outer conductor 206, so that the field shaping element 902 is electrically connected to the outer conductor 206 along its length. Electrical connection between the field shaping element 902 and the outer conductor 206 may be ensured by securing the field shaping element 902 to the outer conductor 206, e.g. using conductive epoxy, or by soldering or welding them together. In some embodiments (not shown) the field shaping element 902 may be integrally formed with the outer conductor 206. The field shaping element 902 acts to increase an effective thickness of the outer conductor 206 in a distal region of the coaxial feed cable 202.

Figure 16:
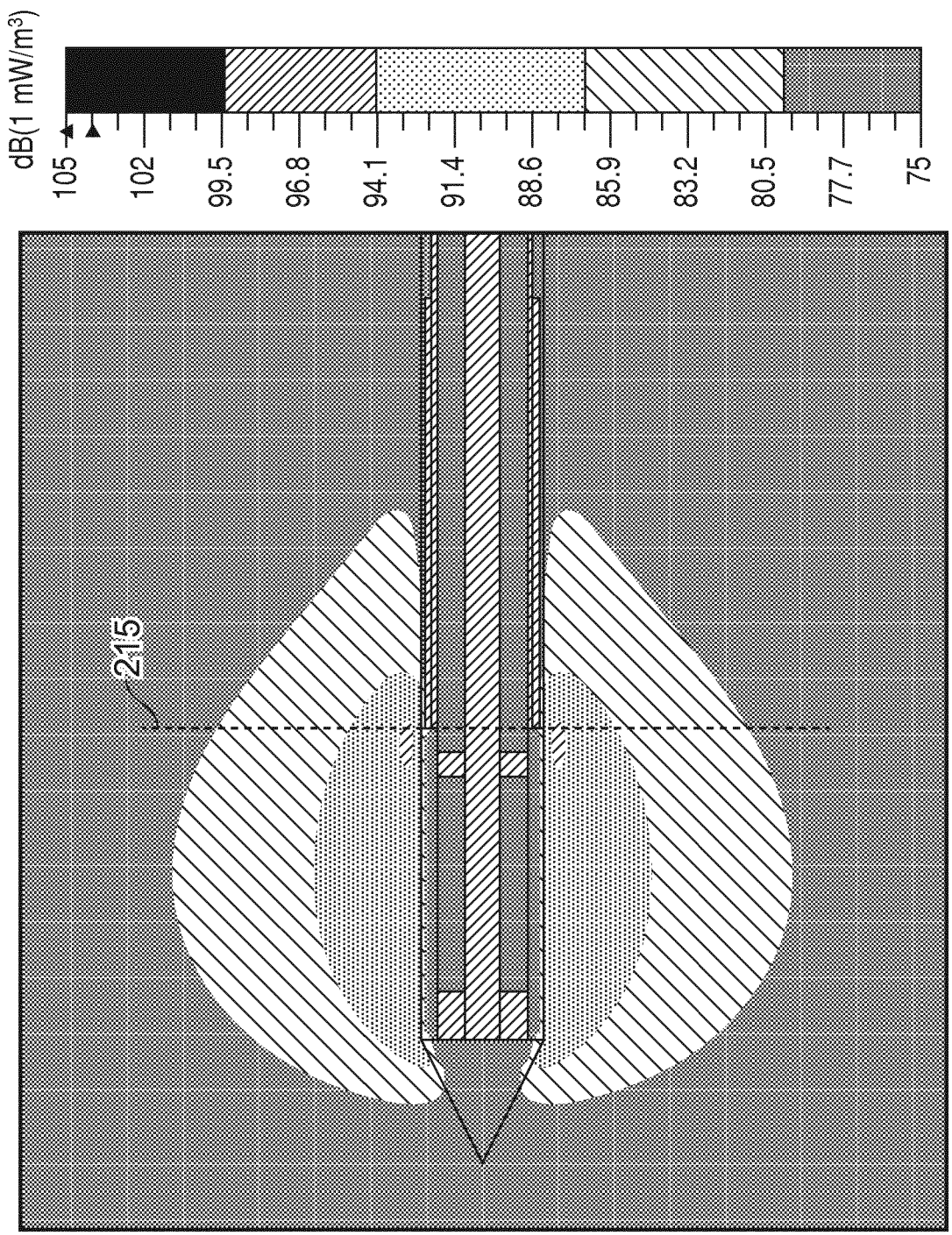
FIG. 16 is a diagram showing a simulated radiation profile for the electrosurgical instrument of FIG. 15.

FIG. 16 shows a simulated microwave radiation profile in target tissue for the electrosurgical instrument 900 illustrated in FIG. 15. The radiation profile was simulated for a microwave frequency of 5.8 GHZ, using finite element analysis software. As can be seen by comparing FIGS. 16 and 14, the radiation profile in FIG. 16 has a smaller tail extending back down the coaxial feed cable. The radiation profile in FIG. 16 also appears more spherical, and is more concentrated around the radiating tip. The only difference between the electrosurgical instrument in FIG. 14 and electrosurgical instrument 900 is the presence of the field shaping element 902 in electrosurgical instrument 900. Thus, field shaping element 902 serves to reduce the tail in the radiation profile, and to concentrate emission of microwave energy around the radiating tip.

The invention claimed is:

1. An electrosurgical instrument comprising:
a coaxial feed cable for conveying microwave energy, the coaxial feed cable having an inner conductor, an outer conductor, and a dielectric material separating the inner conductor and the outer conductor; and
a radiating tip disposed at a distal end of the coaxial feed cable to receive the microwave energy, the radiating tip comprising:
an elongate conductor electrically connected to the inner conductor and extending in a longitudinal direction to form a microwave radiator;
a proximal tuning element electrically connected to the elongate conductor in a proximal region of the radiating tip;
a distal tuning element electrically connected to the elongate conductor in a distal region of the radiating tip; and
a dielectric body disposed around the elongate conductor, the proximal tuning element and the distal tuning element;
a conductive field shaping element disposed at a distal end of the coaxial feed cable, the conductive field shaping element being electrically connected to the outer conductor along a full length of the conductive field shaping element to increase an effective thickness of the outer conductor;
wherein the proximal tuning element and the distal tuning element are spaced apart in the longitudinal direction, whereby a microwave field emitted by the microwave radiator is shaped around the dielectric body; and
wherein a length of the distal tuning element in the longitudinal direction is greater than a length of the proximal tuning element in longitudinal direction.

2. An electrosurgical instrument according to claim 1, wherein the proximal tuning element and the distal tuning element are symmetrical with respect to the longitudinal direction.

3. An electrosurgical instrument according to claim 1, wherein the proximal tuning element and the distal tuning element are cylindrical, and have a central axis that is collinear with a longitudinal axis of the elongate conductor.

4. An electrosurgical instrument according to claim 1, wherein the proximal tuning element is spaced from the distal end of the coaxial feed cable in the longitudinal direction.

5. An electrosurgical instrument according to claim 4 comprising a dielectric element mounted between the proximal tuning element and a distal end of the coaxial feed cable.

6. An electrosurgical instrument according to claim 5, wherein the dielectric element comprises a distal portion of the dielectric material of the coaxial feed cable that protrudes beyond a distal end of the outer conductor.

7. An electrosurgical instrument according to claim 1, wherein the proximal tuning element and the distal tuning element each comprise a channel through which the elongate conductor extends.

8. An electrosurgical instrument according to claim 1, wherein the distal tuning element is located at a distal end of the elongate conductor.

9. An electrosurgical instrument according to claim 1, wherein the elongate conductor is a distal portion of the inner conductor that extends beyond a distal end of the outer conductor.

10. An electrosurgical instrument according to claim 1, wherein the dielectric body comprises a dielectric spacer between the proximal tuning element and the distal tuning element.

11. An electrosurgical instrument according to claim 1, wherein the dielectric body comprises a dielectric sheath that surrounds an outer surface of the proximal tuning element and the distal tuning element.

12. An electrosurgical instrument according to claim 11, wherein an outer surface of the dielectric sheath is flush with an outer surface of the coaxial feed cable at an interface between the coaxial feed cable and the radiating tip.

13. An electrosurgical instrument according to claim 1, wherein the radiating tip further includes a distal tip mounted at a distal end of the elongate conductor, the distal tip being made of a dielectric material.

14. An electrosurgical instrument according to claim 13, wherein the distal tip is pointed.

15. An electrosurgical instrument according to claim 1, wherein the conductive field shaping element is formed by a distal portion of the outer conductor having an increased thickness compared to a proximal portion of the outer conductor.

16. An electrosurgical instrument according to claim 1, wherein the conductive field shaping element has a length in the longitudinal direction corresponding to a quarter wavelength of the microwave energy.

17. An electrosurgical apparatus for treating biological tissue, the electrosurgical apparatus comprising:
    an electrosurgical generator arranged to supply microwave energy; and
    an electrosurgical instrument according to claim 1 connected to receive the microwave energy from the electrosurgical generator.

18. An electrosurgical apparatus according to claim 17 further comprising a surgical scoping device that comprises a flexible insertion cord having an instrument channel, wherein the electrosurgical instrument is dimensioned to fit within the instrument channel.

19. An electrosurgical instrument comprising:
    a coaxial feed cable for conveying microwave energy, the coaxial feed cable having an inner conductor, an outer conductor, and a dielectric material separating the inner conductor and the outer conductor; and
    a radiating tip disposed at a distal end of the coaxial feed cable to receive the microwave energy, the radiating tip comprising:
        an elongate conductor electrically connected to the inner conductor and extending in a longitudinal direction to form a microwave radiator;
        a proximal tuning element electrically connected to the elongate conductor in a proximal region of the radiating tip;
        a distal tuning element electrically connected to the elongate conductor in a distal region of the radiating tip; and
        a dielectric body disposed around the elongate conductor, the proximal tuning element and the distal tuning element;
    wherein the proximal tuning element and the distal tuning element are spaced apart in the longitudinal direction, whereby a microwave field emitted by the microwave radiator is shaped around the dielectric body; and
    wherein a length of the distal tuning element in the longitudinal direction is twice or more than a length of the proximal tuning element in the longitudinal direction.

* * * * *

UNITED STATES PATENT AND TRADEMARK OFFICE
CERTIFICATE OF CORRECTION

PATENT NO. : 12,064,175 B2
APPLICATION NO. : 17/256588
DATED : August 20, 2024
INVENTOR(S) : Christopher Paul Hancock et al.

It is certified that error appears in the above-identified patent and that said Letters Patent is hereby corrected as shown below:

On the Title Page

The filing date of the PCT Application:
Item (22), delete "Jul." and substitute therefor -- Jun. --

Signed and Sealed this
First Day of October, 2024

Katherine Kelly Vidal
Director of the United States Patent and Trademark Office